United States Patent
Matsuguma et al.

(10) Patent No.: US 9,329,118 B2
(45) Date of Patent: May 3, 2016

(54) ENVIRONMENTAL CHAMBER

(71) Applicant: ESPEC CORP., Osaka-shi, Osaka (JP)

(72) Inventors: Osamu Matsuguma, Osaka (JP); Kensuke Akamatsu, Kobe (JP)

(73) Assignee: ESPEC CORP., Osaka (JP)

( * ) Notice: Subject to any disclaimer, the term of this patent is extended or adjusted under 35 U.S.C. 154(b) by 242 days.

(21) Appl. No.: 14/089,257

(22) Filed: Nov. 25, 2013

(65) Prior Publication Data

US 2014/0150574 A1    Jun. 5, 2014

(30) Foreign Application Priority Data

Nov. 30, 2012   (JP) ................. 2012-263001

(51) Int. Cl.
*G01N 17/00*    (2006.01)
*F24F 5/00*    (2006.01)

(52) U.S. Cl.
CPC ..................... *G01N 17/002* (2013.01)

(58) Field of Classification Search
CPC .................. G01N 17/002; G01N 2035/00306; G01N 2203/022
USPC .......................................................... 73/865.6
See application file for complete search history.

(56) References Cited

U.S. PATENT DOCUMENTS

| | | | |
|---|---|---|---|
| 6,360,621 B1 | 3/2002 | Eldred et al. | |
| 7,856,335 B2* | 12/2010 | Morello | A61M 1/122 600/423 |
| 2011/0213501 A1 | 9/2011 | Jin et al. | |

FOREIGN PATENT DOCUMENTS

| | | |
|---|---|---|
| CN | 102197266 | 9/2011 |
| JP | SHO 61-97775 | 12/1984 |
| JP | H01102281 | 4/1989 |
| JP | 3-54738 | 5/1991 |
| JP | H0727374 | 1/1995 |
| JP | H09329566 | 12/1997 |
| JP | 2957903 | 7/1999 |
| JP | 2975601 | 9/1999 |
| TW | 552412 | 9/2003 |

OTHER PUBLICATIONS

Japanese Patent Application No. 2012-263001—Office Action issued Dec. 17, 2014.

* cited by examiner

*Primary Examiner* — Peter Macchiarolo
*Assistant Examiner* — Anthony W Megna Fuentes
(74) *Attorney, Agent, or Firm* — Gerald E. Hespos; Michael J. Porco; Matthew T. Hespos

(57) ABSTRACT

An environmental chamber includes a testing tub in which a testing space is formed. The testing tub has a front wall, a left sidewall, a right sidewall, a rear wall, and a ceiling part, and is divided into a lower tub part and an upper tub part by a dividing surface extended in a direction inclined downwardly and frontwardly. The left and right sidewalls are respectively divided into two portions by the dividing surface. An inner surface of the upper tub part includes at least a part of an inner surface of each of the ceiling part, the front wall, the left sidewall, and the right sidewall. The upper tub part is supported by the lower tub part to be able to open the testing space.

9 Claims, 11 Drawing Sheets

ENVIRONMENTAL CHAMBER

BACKGROUND OF THE INVENTION

1. Field of the Invention

The present invention relates to an environmental chamber.

2. Description of the Related Art

Conventionally, environmental chambers that include a testing tub in which a testing space for arranging a specimen is formed are known, as disclosed in Japanese Patent No. 2975601, Japanese Patent No. 2957903, and Japanese Utility Model Application Laid-open No. H3-54738. The testing tub has a front wall, a left sidewall, a right sidewall, a rear wall, and a ceiling part. According to the environmental chamber disclosed in Japanese Patent No. 2975601, a front wall, a left sidewall, a right sidewall, and a rear wall are divided into upper and lower portions by a dividing surface extended to a horizontal direction. The lower portion of the testing tub is provided with a specimen table on which a specimen is arranged, and the upper portion of the testing tub functions as an upper lid. According to the environmental chamber disclosed in Japanese Patent No. 2957903, front end parts of a left sidewall and a right sidewall are formed in inclined shapes such that lower sides are protruded to a front side, and a front wall is configured as a door that is arranged to be brought into contact with the front end parts of the left sidewall and the right sidewall. The environmental chamber disclosed in Japanese Utility Model Application Laid-open No. H3-54738 has a rectangular parallelepiped testing tub of which a front wall is configured as an outer door, and an inner door is arranged at a further inside of the outer door.

According to the environmental chamber disclosed in Japanese Patent No. 2975601, the testing tub is divided into the upper and lower portions by the dividing surface extended to a horizontal direction. Therefore, when the testing space is opened by swinging the upper lid, an operator performs adjustment work to a specimen such as wiring to the specimen, by inserting a hand from above into the tub. In this case, the operator normally performs the work by standing in front of the testing tub. Therefore, front upper parts of the left and right sidewalls interrupt the work sometimes. On the other hand, according to the environmental chamber disclosed in Japanese Patent No. 2957903, the front end parts of the left sidewall and the right sidewall are formed in inclined shapes such that the lower sides are protruded to the front, and the front wall is configured as a door. Therefore, when the testing space is opened by swinging the front wall, the operator performs adjustment work to a specimen and the like by inserting a hand from the front into the tub. Consequently, when the testing tub is large, the operator can easily perform the adjustment work. However, when the testing tub is small or is set at a low position, the adjustment work becomes cumbersome. This point is similarly applied to the environmental chamber disclosed in Japanese Utility Model Application Laid-open No. H3-54738.

SUMMARY OF THE INVENTION

An object of the present invention is to provide an environmental chamber capable of suppressing adjustment work to a specimen arranged in a testing tub from becoming cumbersome even when the testing tub is small or is located at a low position.

An environmental chamber according to one aspect of the present invention includes a testing tub in which a testing space for arranging a specimen is formed. The testing tub has a front wall, a left sidewall, a right sidewall, a rear wall, and a ceiling part, and is divided into a lower tub part and an upper tub part by a dividing surface extended in a direction inclined downwardly and frontwardly. The left sidewall and the right sidewall are respectively divided into two portions by the dividing surface. An inner surface of the upper tub part includes at least a part of an inner surface of each of the ceiling part, the front wall, the left sidewall, and the right sidewall. A rear end part of the dividing surface is positioned at a rear side of a center of the ceiling part in a front and rear direction thereof. The upper tub part is supported by the lower tub part to be able to open the testing space.

DESCRIPTION OF THE PREFERRED EMBODIMENTS

Hereinafter, an embodiment of the present invention is described in detail with reference to the drawings.

Figure 1:
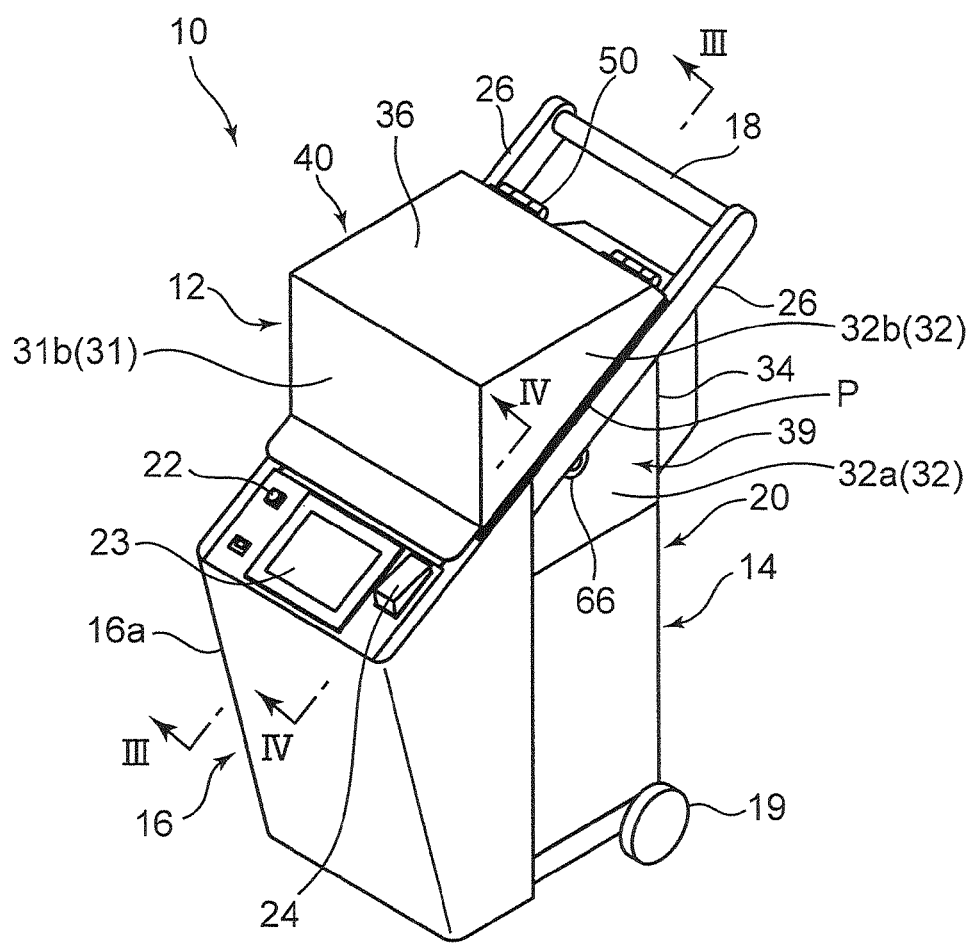
FIG. 1 is a perspective view of an environmental chamber according to an embodiment of the present invention in a state that an upper tub part is at a closed position.
Figure 2:
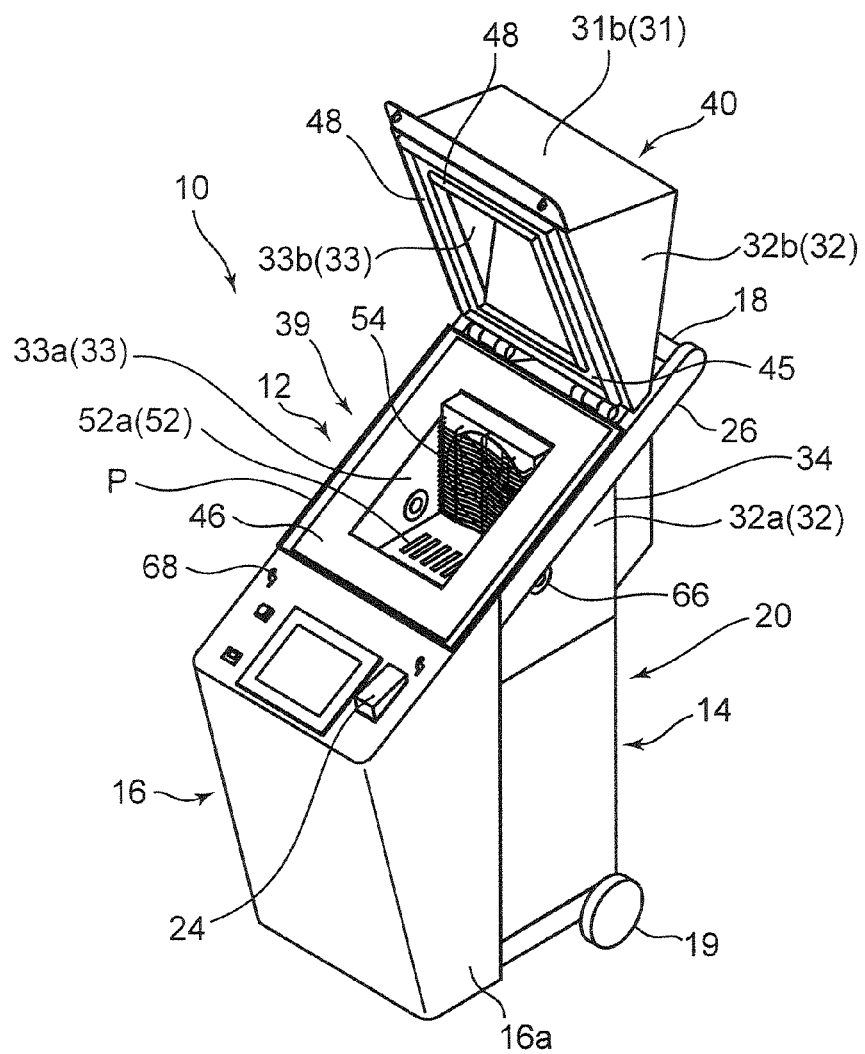
FIG. 2 is a perspective view of the environmental chamber in a state that an upper tub part is at an opened position.

As shown in FIGS. 1 and 2, an environmental chamber 10 according to an embodiment of the present invention includes a testing tub 12, a machine chamber 14 that is arranged at a lower side of the testing tub 12, and an electrical equipment part 16 that is arranged at a front side of the machine chamber 14. Also, in the environmental chamber 10, there are provided a handlebar 18 that is arranged at a rear side of the testing tub 12, and wheels 19 that are arranged at a lower end part of an outer covering body 20 including the testing tub 12 and the machine chamber 14.

Figure 3:
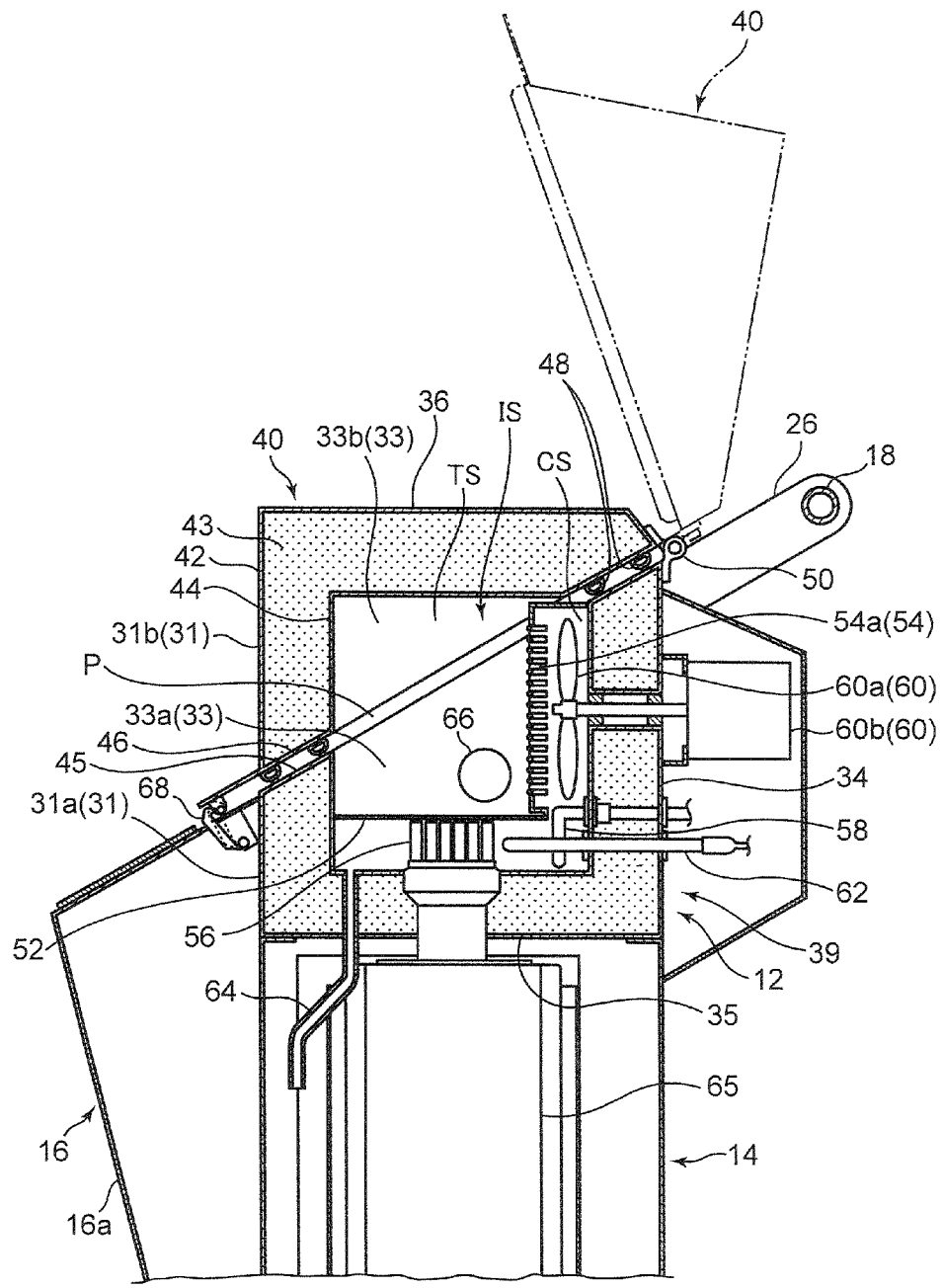
FIG. 3 is a partial cross-sectional view along a line III-III in FIG. 1.

As shown in FIG. 3, the testing tub 12 and the machine chamber 14 are arranged in an up and down direction, and they are formed as a main body having a longitudinal rectangular parallelepiped shape as a whole. The electrical equipment part 16 is provided to be protruded from the main body to a front side. An outer surface of the electrical equipment part 16 is configured by having a front cover 16*a* fitted to the main body so that an inside of the electrical equipment part 16 becomes hollow. A control device and the like not shown are provided in an internal space formed between the front cover 16*a* and the main body.

An upper surface of the electrical equipment part 16 has a surface inclined downwardly and frontwardly. Switches 22, an operation screen 23, an unlock button 24, and the like are arranged on the upper surface of the electrical equipment part 16, as shown in FIG. 1. The handlebar 18 is provided at rear end parts of frame members 26 that are extended along left and right side surfaces of the testing tub 12 along an inclined surface approximately in flush with the upper surface of the electrical equipment part 16. The frame members 26 are extended from a rear surface of the testing tub 12 to a further rear side. The handlebar 18 is provided to be bridged between the rear end parts of the frame members 26. That is, the handlebar 18 is provided at a position protruded to a rear side of the testing tub 12. The wheels 19 are also provided at a lower end part of a rear part of the outer covering body 20. Therefore, by turning the environmental chamber 10 to incline backward the outer covering body 20 and lift a lower end of the front end part of the outer covering body 20, the environmental chamber 10 can be easily moved, when the environmental chamber 10 is pushed by grasping the handlebar 18 in this state.

As shown in FIG. 3, the testing tub 12 includes a front wall 31, a left sidewall 32, a right sidewall 33, a rear wall 34, a bottom surface part 35, and a ceiling part 36, and is formed in a rectangular parallelepiped shape as a whole. An internal space IS is formed in the testing tub 12. The internal space IS includes a testing space TS in which a specimen is arranged, and an air-conditioning space CS which is communicated with the testing space TS and in which air supplied to the testing space TS is temperature-regulated. The internal space IS and the testing space TS are formed in an approximately rectangular parallelepiped shape. The air-conditioning space CS is not required to be formed as a part of the internal space IS in the testing tub 12. For example, the air-conditioning space CS may be configured to be formed at an outside of the testing tub 12 and communicated with the testing space TS that is formed in the testing tub 12 via a through-path not shown that pierces through the testing tub 12.

The testing tub 12 is divided into a lower tub part 39 and an upper tub part 40 by a planar dividing surface P that is extended in a direction inclined downwardly and frontwardly. The internal space IS (the testing space TS) includes a lower space (a lower testing space) that is positioned in the lower tub part 39 and an upper space (an upper testing space) that is positioned in the upper tub part 40. A front end part of the dividing surface P is positioned at a lower side than a center in a height direction of the front wall 31 of the testing tub 12, and a rear end part of the dividing surface P is positioned at a rear side of a center in a front and rear direction of the ceiling part 36. The dividing surface P of the example in the drawings passes vicinity of an intersection of a lower surface of the ceiling part 36 and a front surface of the rear wall 34, and the rear end part of the dividing surface P is positioned near an upper end part of a rear surface (an outer surface) of the rear wall 34.

The lower tub part 39 includes a lower part 31*a* of the front wall 31, a lower part 32*a* of the left sidewall 32, a lower part 33*a* of the right sidewall 33, the rear wall 34, and the bottom surface part 35. On the other hand, the upper tub part 40 includes an upper part 31*b* of the front wall 31, an upper part 32*b* of the left sidewall 32, an upper part 33*b* of the right sidewall 33, and the ceiling part 36. Therefore, the lower space (the lower testing space) has a front surface, a left side surface, a right side surface, a rear surface, and a bottom surface, and an upper surface is opened. The upper space (the upper testing space) has a front surface, a left side surface, a right side surface, and an upper surface, and a lower surface is opened. A plane between the lower space (the lower testing space) and the upper space (the upper testing space) becomes an inclined flat surface that is in flush with the dividing surface P. Therefore, the upper tub part 40 includes an upper end part of the front wall 31, a front upper end part of the left sidewall 32, a front upper end part of the right sidewall 33, and a front end part of the ceiling part 36.

The lower part 31*a* of the front wall 31 is not visible from an outside because the lower part 31*a* is covered with the front cover 16*a*. However, a configuration is not limited to that described above. For example, the front cover 16*a* may be configured to cover a front surface of only the machine chamber 14.

The front wall 31, the left sidewall 32, the right sidewall 33, the rear wall 34, the bottom surface part 35, and the ceiling part 36 are respectively configured to include an outer wall plate 42 made of a metal plate and the like, an inner wall plate 44 made of a metal plate and the like arranged with a distance from the outer wall plate 42, and a heat insulation material 43 provided between the outer wall plate 42 and the inner wall plate 44. An inclined upper surface of the lower tub part 39 facing the dividing surface P and an inclined lower surface of the upper tub part 40 facing the dividing surface P are respectively arranged with thin plates 45 and 46, to prevent exposure of the heat insulation material 43. The thin plates 45 and 46 are respectively configured by a metal or a resin having a high heat insulation characteristic. A packing 48 for air-tight sealing the internal space IS from an outside is arranged between the thin plate 45 that configures the inclined upper surface and the thin plate 46 that configures the inclined lower surface. The packing 48 is fixed to the thin plate arranged at an inclined-upper surface side. In the present embodiment, the packing 48 is a double packing 48.

The upper tub part 40 is supported by the lower tub part 39 to be able to open the internal space IS (the testing space TS). Specifically, the testing tub 12 is provided with hinges 50 to connect an outer surface of the rear wall 34 with an outer surface of the ceiling part 36. The upper tub part 40 is supported by the lower tub part 39 swingably around the hinges 50.

As described above, the internal space IS includes the testing space TS and the air-conditioning space CS. The testing space TS is formed in approximately a rectangular parallelepiped shape, and the air-conditioning space CS has a lower part positioned at a lower side of the testing space TS and a rear part positioned at a rear side of the testing space TS. On a lower surface of the testing space TS, a mounting plate 52 formed with slits 52*a* is arranged. The testing space TS and the lower part of the air-conditioning space CS are partitioned via the mounting plate 52. The specimen is mounted on the mounting plate 52. Air in the testing space TS flows into the lower part of the air-conditioning space CS through the slits 52*a*. At the rear surface side of the testing space TS, a meshed grill 54 having many through-holes 54*a* is arranged. The testing space TS and the rear part of the air-conditioning space CS are partitioned via the grill 54. Air in the rear part of the air-conditioning space CS flows into the testing space TS through the through-holes 54*a* of the grill 54.

In the air-conditioning space CS, there are arranged a fin 56 as a cooling unit, a heater 58 as heating means, an impeller 60*a* of a fan 60 as an air blowing unit, a temperature sensor 62 as temperature detecting means, and a drain pipe 64 for draining water pooled in the internal space IS. The fin 56 is provided at an upper part of a stirling refrigeration machine 65 arranged in the machine chamber 14, and is also arranged in a lower part of the air-conditioning space CS. The fin 56 is cooled by cold air generated by the stirling refrigeration machine 65. With this configuration, by absorbing heat from air in the air-conditioning space CS, the air is cooled. A refrigeration machine for absorbing heat is not limited to the stirling refrigeration machine.

The heater 58 pierces through the rear wall 34 of the lower tub part 39, and a heating unit is arranged in the lower part of the air-conditioning space CS. The heater 58 is configured to have a heating amount thereof controlled by a controller not shown.

The fan 60 has the impeller 60a and a motor 60b for rotating the impeller 60a. The motor 60b is fixed to the outer surface of the rear wall 34 of the lower tub part 39. A drive shaft of the motor 60b is positioned in the rear part of the air-conditioning space CS by piercing through the rear wall 34. The impeller 60a is fixed to the drive shaft.

The temperature sensor 62 is arranged in the lower part of the air-conditioning space CS, and is configured to detect a temperature of the air in the air-conditioning space CS. The temperature sensor 62 is also used to monitor whether a temperature of the air detected by the temperature sensor 62 exceeds a threshold value set in advance.

A through-hole is provided in each of the left sidewall 32 (the lower part 32a) and the right sidewall 33 (the lower part 33a) of the lower tub part 39, and a cap 66 is detachably covered on each through-hole. Through the through-hole, the specimen in the testing space TS can be wired.

Figure 4:
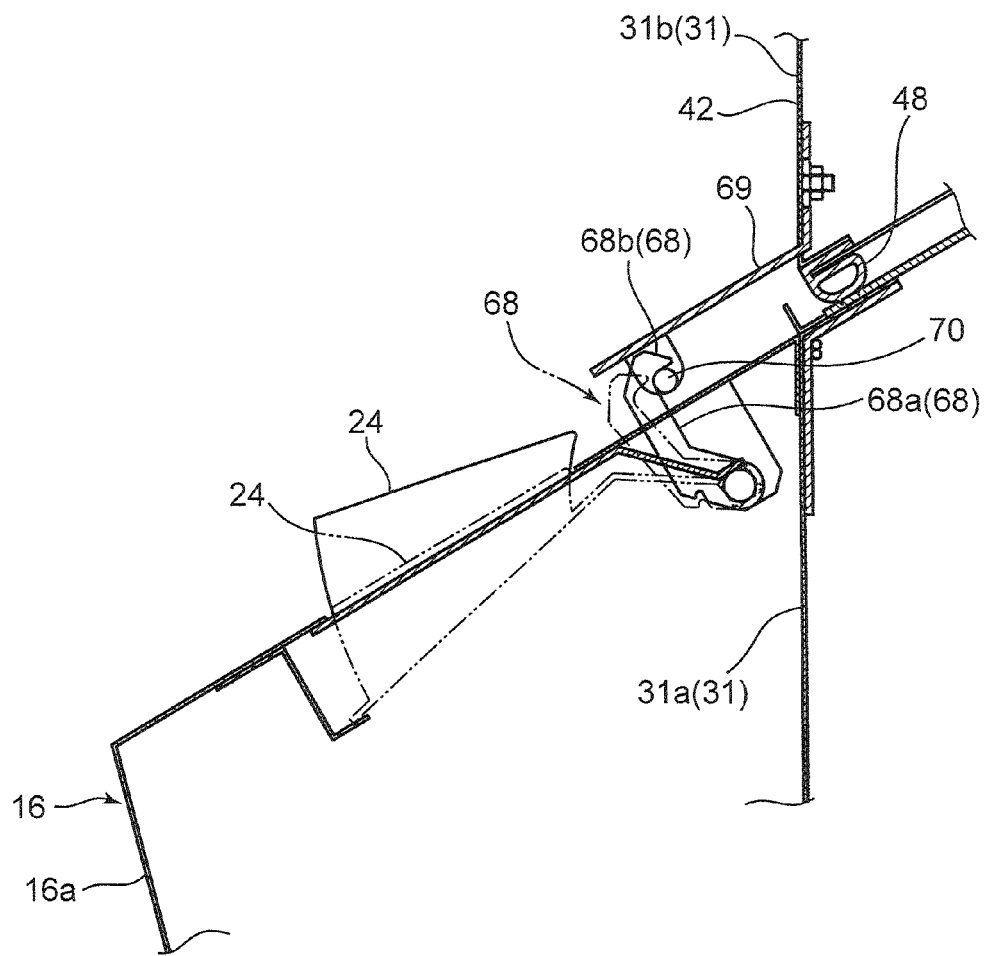
FIG. 4 is a partial cross-sectional view along a line IV-IV in FIG. 1.

The environmental chamber 10 is provided with a locking member 68 for locking the upper tub part 40, and an unlock button 24 for unlocking the upper tub part 40 that is locked by the locking member 68. As shown in FIG. 4, the locking member 68 has a turning part 68a swingably supported by the outer covering body 20, and a pawl 68b formed at a front end part of the turning part 68a. The locking member 68 can take a locked position (a position indicated by a solid line in FIG. 4) where the pawl 68b is locked to a locked part 70, and an unlocked position (a position indicated by a two-dot chain line in FIG. 4) where the pawl 68b is separated from the locked part 70. The locked part 70 is fixed to a plate 69 stretched from the front wall 31 of the upper tab part 40 to a front side.

The unlock button 24 is an operating part for moving the locking member 68 from the locked position to the unlocked position, and is arranged on the upper surface of the electrical equipment part 16. The unlock button 24 is configured to move integrally with the locking member 68. When the unlock button 24 is at a position (a position indicated by the solid line in FIG. 4) where the unlock button 24 is protruded from the upper surface of the electrical equipment part 16, the locking member 68 becomes at the locked position. On the other hand, when the unlock button 24 is at a position (a position indicated by the two-dot chain line in FIG. 4) where the unlock button 24 is pressed into the electrical equipment part 16, the locking member 68 becomes at the unlocked position. Therefore, by pressing the unlock button 24, the locking member 68 can be moved from the locked position to the unlocked position. With this configuration, the upper tub part 40 is unlocked, and the upper tub part 40 can be swung upward.

As described above, in the present embodiment, the left sidewall 32 and the right sidewall 33 of the testing tub 12 are divided into the lower tub part 39 and the upper tub part 40 by the dividing surface P that is extended in a downwardly and frontwardly inclined direction. Therefore, when the testing space TS is opened by moving the upper tub part 40 from the lower tub part 39, front upper parts of the left sidewall 32 and the right sidewall 33 and a front part of the ceiling part 36 as parts of the upper tub part 40 move to positions separated above from the lower tub part 39. Because the rear end part of the dividing surface P is positioned at a rear side of the center of the ceiling part 36 in the front and rear direction, in performing adjustment work to the specimen arranged in the testing space TS in a state that the testing space TS is opened, the operator can perform the adjustment work by inserting a hand from above into the lower tub part 39. Consequently, the adjustment work to the specimen can be suppressed from becoming cumbersome even when the testing tub 12 is small or is set at a low position. Further, at this time, because the front upper parts of the left sidewall 32 and the right sidewall 33 are at positions separated from the lower tub part 39, the front upper parts of the left sidewall 32 and the right sidewall 33 do not interrupt the work, even when the operator works by standing in front of the testing tub 12. Therefore, it becomes possible to suppress the adjustment work to the specimen arranged in the testing space TS from becoming cumbersome.

Further, in the present embodiment, because the front end part of the dividing surface P is positioned at a lower side than the center in the height direction of the front wall 31, a portion at a higher side than the center in the height direction of the front wall 31 is included in the upper tub part 40. As a result, when the testing space TS is opened by moving the upper tub part 40 from the lower tub part 39, the upper end of the front wall 31 included in the lower tub part 39 becomes low. Therefore, a work load of the operator positioned in front of the testing tub 12 can be more reduced when performing the adjustment work to the specimen.

In the present embodiment, the handlebar 18 is provided at the rear side of the testing tub 12, and the wheels 19 are also arranged at the lower end part of the rear surface of the outer covering body 20. Therefore, the operator can easily move the testing tub 12 by pushing the testing tub 12 by grasping the handlebar 18 in a state of the testing tub 12 being inclined to a rear side.

The present invention is not limited to the above embodiment, and can be variously modified and improved within a range not deviating from the significance of the invention.

Figure 5:
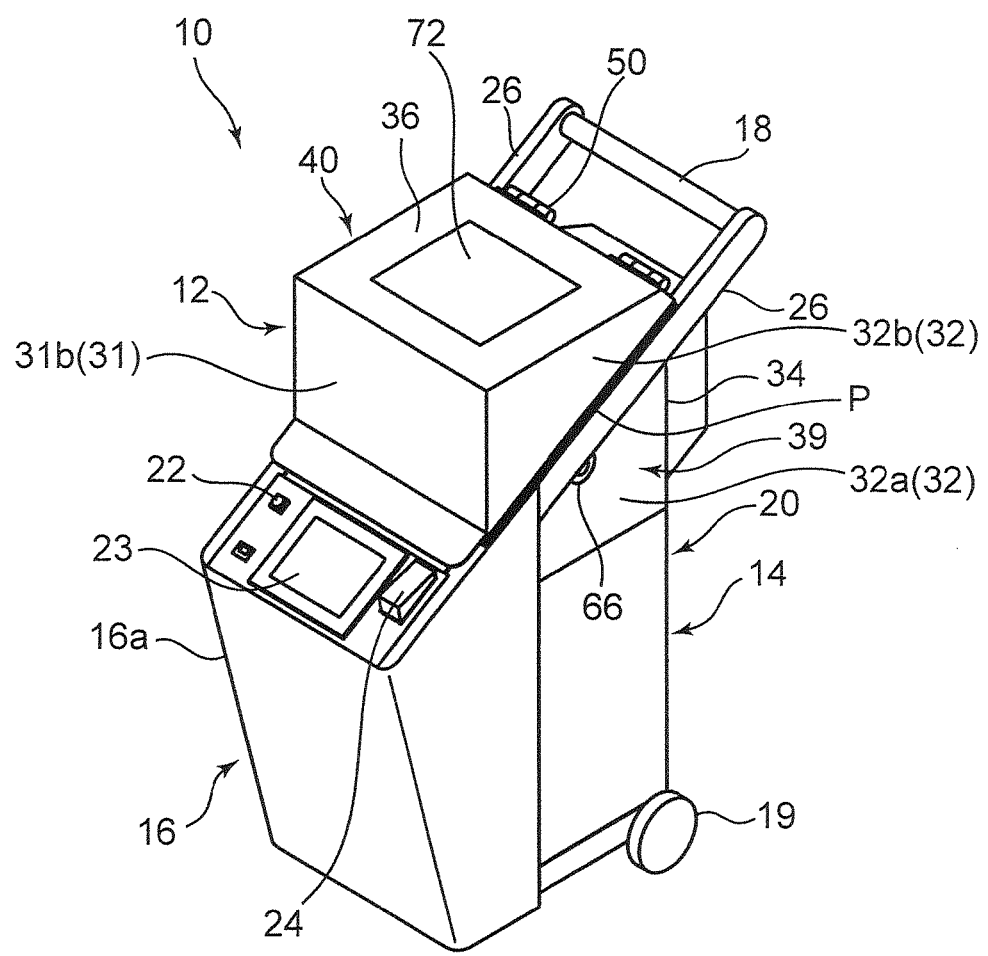
FIG. 5 is a perspective view of an environmental chamber according to another embodiment of the present invention.
Figure 6:
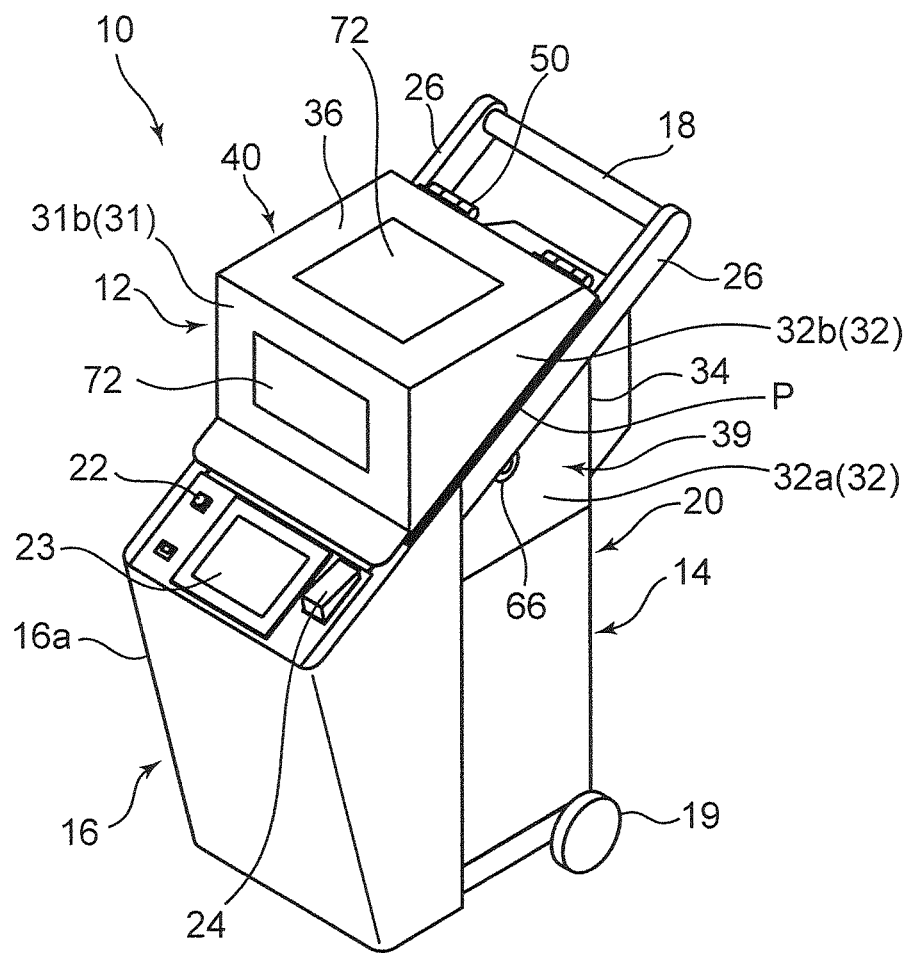
FIG. 6 is a perspective view of an environmental chamber according to still another embodiment of the present invention.

In the above embodiment, the environmental chamber is configured such that the internal space IS cannot be seen from the outer wall plate 42 of the upper tub part 40. However, a configuration is not limited to the above. For example, as shown in FIG. 5, the environmental chamber may be configured to have a transparent plate 72 embedded into the ceiling part 36 of the upper tub part 40 so that the internal space IS (the testing space TS) can be observed through the transparent plate 72. Alternatively, as shown in FIG. 6, the environmental chamber may be configured to have the transparent plate 72 embedded into each of the ceiling part 36 of the upper tub part 40 and the upper part 31b of the front wall 31 so that the internal space IS (the testing space TS) can be observed through these transparent plates 72. The transparent plate 72 may be configured to be embedded into only the front wall 31.

Figure 7:
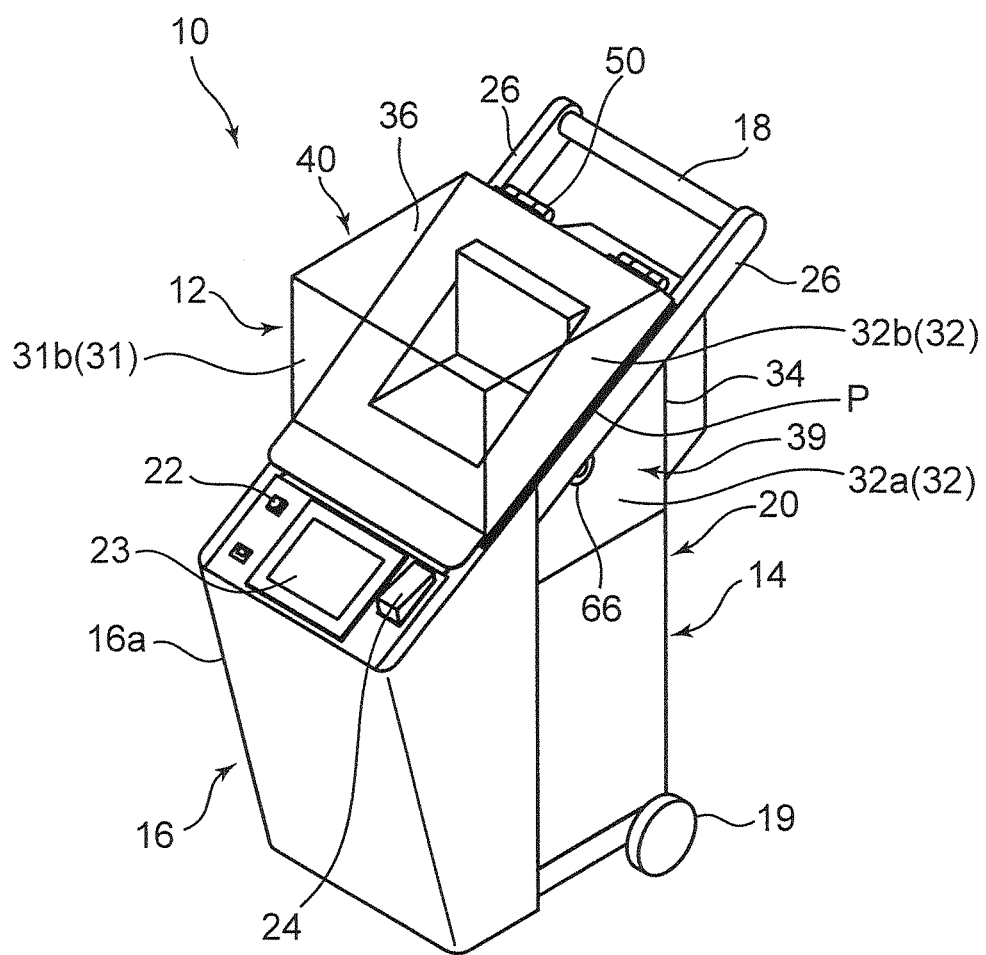
FIG. 7 is a perspective view of an environmental chamber according to still another embodiment of the present invention.

Alternatively, as shown in FIG. 7, the upper tub part 40 may be configured by a transparent member. In this case, an internal state of the testing space TS can be also observed from the upper tub part 40.

Figure 8:
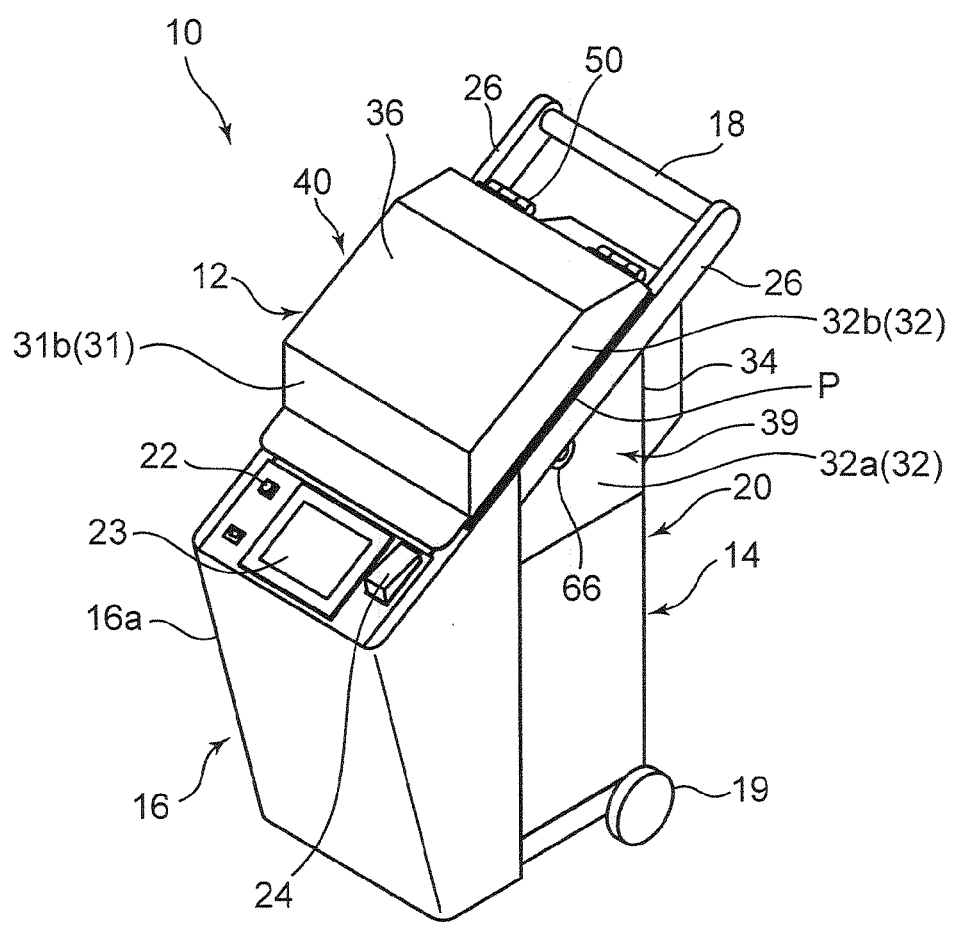
FIG. 8 is a perspective view of an environmental chamber according to still another embodiment of the present invention.

In the above embodiment, although the upper surface of the ceiling part 36 is configured to be horizontal, a configuration is not limited to this. For example, as shown in FIG. 8, the upper surface of the ceiling part 36 may be configured to be inclined downwardly and frontwardly.

In the above embodiment, although the environmental chamber is configured to be provided with the handlebar 18 and the wheels 19, the environmental chamber may be configured to omit the handlebar 18 and the wheels 19.

Figure 9:
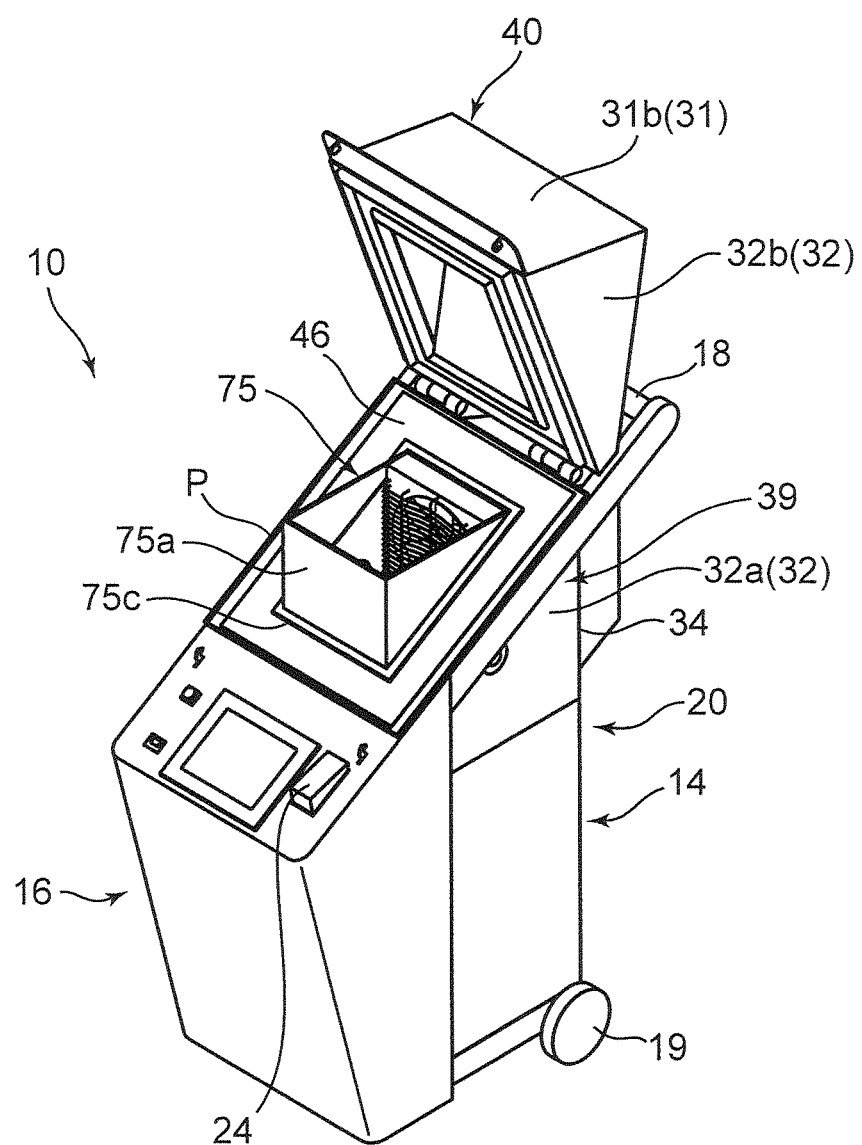
FIG. 9 is a perspective view of an environmental chamber according to still another embodiment of the present invention.

The environmental chamber 10 may be configured to include an internal tub body 75 detachably mounted on the lower tub part 39 as shown in FIG. 9. The internal tub body 75 has a sidewall part 75a along inner surfaces of portions (the upper parts 32b and 33b) included in the upper tub part 40 in the front wall 31, the left sidewall 32, and the right sidewall 33. Lower end surfaces of the sidewall part 75a at both left and right sides are inclined to correspond to an inclined direction of the dividing surface P. The internal tub body 75 is mounted on the lower tub part 39 to surround the upper testing space. However, even when the upper tub part 40 is rotated and the testing space TS is in an opened state, the internal tub body 75 does not follow the upper tub part 40, but is left on the lower tub part 39.

Figure 10A:
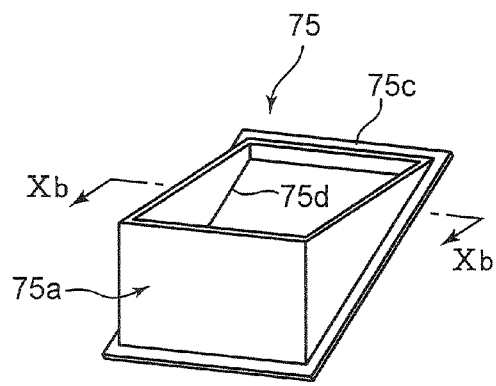
FIG. 10A is a perspective view of an internal tub body of which an upper surface is open.
Figure 10B:
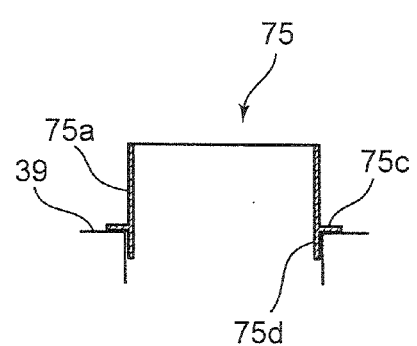
FIG. 10B is a cross-sectional view along a line Xb-Xb in FIG. 10A.

As shown in FIGS. 10A and 10B, the sidewall part 75a of the internal tub body 75 is formed with outward protruded parts 75c that are protruded outward, and downward protruded parts 75d that are protruded downward from a lower end part of the sidewall part 75a. A width of the sidewall part 75a (a length in a left and right direction of the internal tub body 75) is formed slightly smaller than a width of a space in the lower tub part 39. Therefore, the outward protruded parts 75c are mounted on the upper surface of the lower tub part 39, and the downward protruded parts 75d enter the lower tub part 39. Alternatively, it may be configured such that a width of the sidewall part 75a (a length in the left and right direction of the internal tub body 75) is formed the same as a width of the space in the lower tub part 39 and that the downward protruded parts 75d are protruded downward at a slightly inner side than the sidewall part 75a. Alternatively, it may be configured such that a width of the sidewall part 75a (a length in the left and right direction of the internal tub body 75) is formed the same as a width of the space in the lower tub part 39 and that the outward protruded parts 75c and the downward protruded parts 75d are omitted. In this case, to enable the internal tub body 75 to be arranged on the lower tub part 39, the space in the upper tub part 40 may be formed to have a slightly larger width than that of the space in the lower tub part 39. Alternatively, the outward protruded parts 75c and the downward protruded parts 75d may be configured to be not provided in a whole periphery.

In the environmental chamber 10, the internal tub body 75 is kept left on the lower tub part 39 even after the testing space TS is opened by moving the upper tub part 40. That is, the internal tub body 75 is arranged to be protruded from the lower tub part 39. Therefore, a space partitioned by the sidewall part 75a of the internal tub body 75 is formed at an upper side of the lower tub part 39. Therefore, when driving the environmental chamber 10 in a state that the upper tub part 40 is moved to open the testing space TS, heat in the space formed by the lower tub part 39 and the internal tub body 75 can be prevented from escaping. Accordingly, even when the upper tub part 40 is in an opened state, it is possible to drive the environmental chamber 10 while observing the specimen arranged in the lower testing space or while checking a trouble of the specimen, for example, in a state that a temperature in the lower testing space does not easily change. In the internal tub body 75, a packing (not shown) may be provided to secure a sealing characteristic in a contact part between the internal tub body 75 and the lower tub part 39. The internal tub body 75 may be configured to have a lower end part thereof embedded into the lower tub part 39. When it is known in advance that the work is to be performed by opening the upper tub part 40 or the like, the internal tub body 75 is set after the specimen is set before starting driving. The driving is performed after the upper tub part 40 is closed. Accordingly, the internal tub body 75 can exist on the lower tub part 39 even when the upper tub part 40 is opened thereafter.

Figure 11:
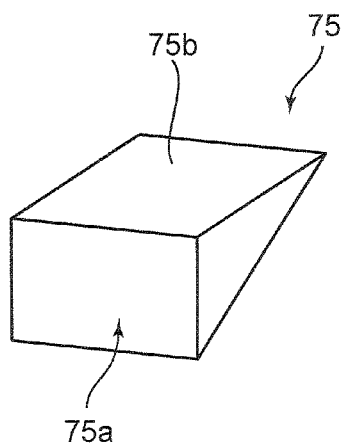
FIG. 11 is a perspective view of an internal tub body having an upper surface part.

Although the internal tub body 75 shown in FIG. 9 is configured to have only the sidewall part 75a and have the upper surface opened as shown in FIG. 10A, a configuration of the internal tub body 75 is not limited to this. As shown in FIG. 11, the internal tub body 75 may be configured to include an upper surface part 75b that is bridged over the upper end part of the sidewall part 75a. In this case, preferably, at least a part of the internal tub body 75 is configured by a transparent material. Because the upper surface of the internal tub body 75 is also blocked in this configuration, heat in the space in the internal tub body 75 cannot easily escape.

A front surface part (a part of the sidewall part 75a) or the upper surface part 75b of the internal tub body 75 may be openably/closably configured. With this configuration, temperature disorder in the internal tub body 75 can be minimized while securing workability. That is, when the upper surface part 75b is openable/closable, temperature disorder in the tub at a low-temperature time can be minimized, and when the front surface part is openable/closable, temperature disorder in the tub at a high-temperature time can be minimized. The internal tub body 75 can be configured by stainless steel, aluminum, or the like, and the transparent material can be configured by polycarbonate, vinyl chloride, or the like. The internal tub body 75 that includes the upper surface part 75b may be also configured to be formed with the outward protruded parts 75c and the downward protruded parts 75d like those shown in FIGS. 10A and 10B.

Figure 12:
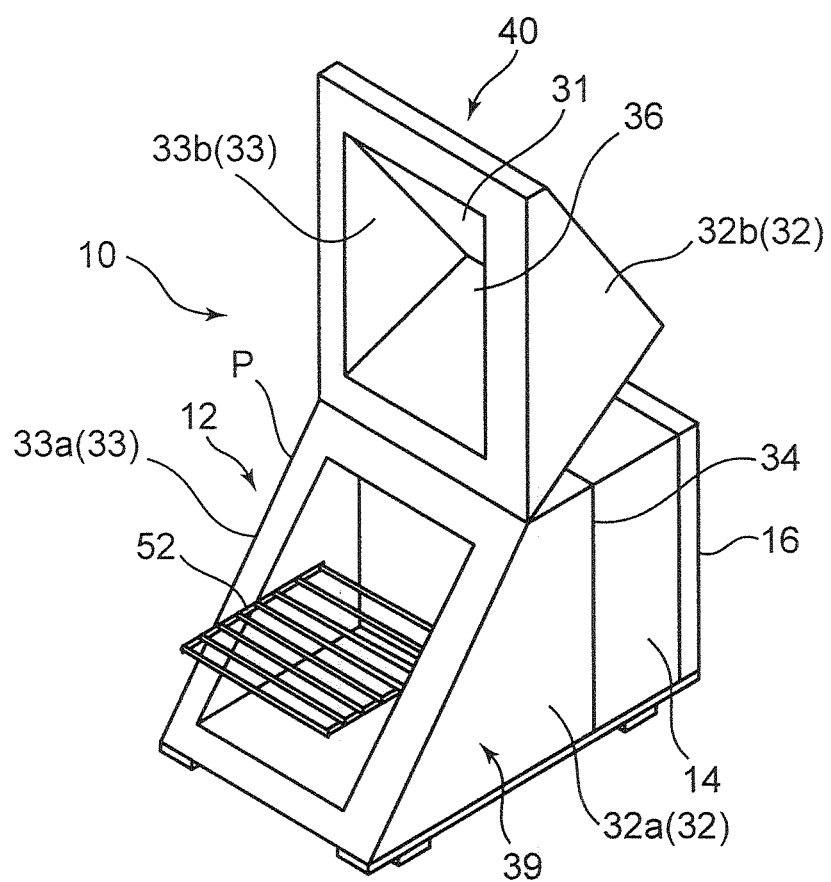
FIG. 12 is a perspective view of an environmental chamber according to still another embodiment of the present invention.

In the above embodiment, although the machine chamber 14 is arranged at the lower side of the testing tub 12, and the electrical equipment part 16 is arranged at the front side of the machine chamber 14, a configuration is not limited to this. Alternatively, as shown in FIG. 12, for example, the machine chamber 14 and the electrical equipment part 16 may be configured to be arranged at a rear side of the approximately rectangular parallelepiped testing tub 12. In a mode shown in FIG. 12, the dividing surface P passes through a lower end part of the front wall 31, and the front wall 31 is not configured to be divided into upper and lower portions. However, in a similar manner to that in the above embodiment, the front wall 31 may be configured to be divided into upper and lower portions and have the lower part 31a and the upper part 31b.

In the above embodiment, the upper tub part 40 is swingably supported by the lower tub part 39. Alternatively, instead of the upper tub part 40 being swingably supported, the upper tub part 40 may be configured to be supported to open the testing space TS by sliding in an up and down direction.

The above embodiment is summarized below.

(1) In the above embodiment, the testing tub is divided at the left sidewall and the right sidewall into the lower tub part and the upper tub part by the dividing surface extended in a direction inclined downwardly and frontwardly. Therefore, when the testing space is opened by moving the upper tub part from the lower tub part, the front upper part of the left sidewall, and the right sidewall as parts of the upper tub part and the front part of the ceiling part as a part of the upper tub part move to positions separated above from the lower tub part. Because the rear end part of the dividing surface is positioned at a rear side of the center of the ceiling part in the front and rear direction, when the operator performs adjustment work to the specimen arranged in the testing space in the state that the testing space is opened, the operator can perform the adjustment work by inserting a hand from above into the lower tub part. Consequently, the adjustment work to the specimen can be suppressed from becoming cumbersome even when the testing tub is small or is set at a low position. Further, at this time, because the front upper parts of the left sidewall and the right sidewall are at positions separated from the lower tub part, the front upper parts of the left sidewall and the right sidewall do not interrupt the work, even when the operator works by standing in front of the testing tub. Therefore, it becomes possible to suppress the adjustment work to the specimen arranged in the testing space from becoming cumbersome.

(2) Preferably, the front end part of the dividing surface is positioned at a lower side than the center of the front wall in the height direction. In this mode, because a part of a lower portion of the front wall than a center in a height direction of the front wall is included in the upper tub part, when the testing space is opened by moving the upper tub part from the lower tub part, the upper end of the front wall included in the lower tub part becomes low. Therefore, a work load of the operator positioned in front of the testing tub can be more reduced when performing the adjustment work to the specimen.

(3) The above environmental chamber may be configured to include an internal tub body detachably arranged on the lower tub part. The internal tub body has a sidewall part along inner surfaces of portions included in the upper tub part in the front wall, the left sidewall, and the right sidewall. Lower end surfaces of the sidewall part may correspond to an inclined direction of the dividing surface. The internal tub body may be configured to exist on the lower tub part even in a state that the upper tub part has moved to open the testing space.

In this mode, even when the testing space is opened by moving the upper tub part, the internal tub body can be left on the lower tub part. Accordingly, a space partitioned by the sidewall part of the internal tub body is formed at an upper side of the lower tub part. Therefore, when driving the environmental chamber in a state that the upper tub part is moved to open the testing space, heat in the space formed by the lower tub part and the internal tub body can be prevented from escaping. Accordingly, it is possible to drive the environmental chamber while observing the specimen arranged in the lower testing space or while checking a trouble of the specimen, for example, in a state that a temperature in the space does not easily change. When performing work other than the test, the internal tub body can be removed. In this case, the work can be performed without interruption.

(4) The upper surface of the internal tub body may be configured to be opened. In this mode, a state of an inside of the internal tub body can be seen through the opened upper surface.

(5) The internal tub body may be configured to include an upper surface part that is bridged over the upper end part of the sidewall part. In this case, at least a part of the internal tub body may be configured by a transparent material. In this mode, a state of an inside of the internal tub body can be seen through a portion configured by the transparent member. Because the upper surface of the internal tub body is also blocked, heat in the space in the internal tub body cannot easily escape.

(6) The above environmental chamber may be configured to further include a handlebar that is protruded to a rear side of the testing tub, and wheels that are arranged at a lower end part of the environmental chamber. In this mode, the operator can easily move the testing tub by pushing the testing tub in a state of the testing tub being inclined to a rear side by grasping the handlebar.

(7) A transparent plate may be configured to be provided in at least one of the ceiling part and the front wall. In this mode, a state of an inside of the testing space can be observed through the transparent plate.

(8) The upper tub part may be configured by a transparent member. In this mode, a state of an inside of the testing space can be observed from the upper tub part.

As described above, according to the environmental chamber in the above embodiment, adjustment work to the specimen arranged in the testing tub can be suppressed from becoming cumbersome even when the testing tub is small or is located at a low position.

This application is based on Japanese Patent application No. 2012-263001 filed in Japan Patent Office on Nov. 30, 2012, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. An environmental chamber comprising a testing tub in which a testing space for arranging a specimen is formed, wherein the testing tub has a front wall, a left sidewall, a right sidewall, a rear wall, and a ceiling part, and is divided into a lower tub part and an upper tub part by a dividing surface extended in a direction inclined down and frontward, the ceiling part having a center in a front to rear direction thereof, the left sidewall and the right sidewall are respectively divided into two portions by the dividing surface, and an inner surface of the upper tub part includes at least a part of an inner surface of each of the ceiling part, the front wall, the left sidewall, and the right sidewall, a rear end part of the dividing surface is positioned at a rear side of the center of the ceiling part in the front to rear direction of the ceiling part, the upper tub part is supported by the lower tub part to be able to open the testing space, and the environmental chamber further comprises an internal tub body arranged detachably on the lower tub part, the internal tub body has a sidewall part along inner surfaces of portions included in the upper tub part in the front wall, the left sidewall, and the right sidewall, and the internal tub body remains on the lower tub part in a state where the upper tub part moves to open the testing space.

2. The environmental chamber according to claim 1, wherein a front end part of the dividing surface is positioned at a lower side than a center of the front wall in a height direction thereof.

3. The environmental chamber according to claim 1, wherein lower end surfaces of the sidewall part are formed correspondingly to an inclined direction of the dividing surface.

4. The environmental chamber according to claim 1, wherein an upper surface of the internal tub body is opened.

5. The environmental chamber according to claim 1, wherein the internal tub body includes an upper surface part that is bridged over an upper end part of the sidewall part, and at least a part of the internal tub body is configured by a transparent material.

6. The environmental chamber according to claim 1, further comprising:
a handlebar protruded to a rear side of the testing tub; and
wheels arranged at a lower end part of the environmental chamber.

7. The environmental chamber according to claim 1, wherein a transparent plate is provided in at least one of the ceiling part and the front wall.

8. The environmental chamber according to claim 1, wherein the upper tub part is configured by a transparent member.

9. An environmental chamber comprising:
a testing tub in which a testing space for arranging a specimen is formed;
frame members extending along left and right side surfaces of the testing tub,
a handlebar provided at rear end parts of the frame members and protruded to a rear side of the testing tub;
wheels arranged at a lower end part of the environmental chamber, wherein
the testing tub has a front wall, a left sidewall, a right sidewall, a rear wall, and a ceiling part, and is divided into a lower tub part and an upper tub part by a dividing surface extended in a direction inclined down and frontward, the ceiling part having a center in a front to rear direction,
the left sidewall and the right sidewall are respectively divided into two portions by the dividing surface, and an inner surface of the upper tub part includes at least a part of an inner surface of each of the ceiling part, the front wall, the left sidewall, and the right sidewall,
a rear end part of the dividing surface is positioned at a rear side of a center of the ceiling part in a front and rear direction thereof,
a front end part of the dividing surface is positioned at a lower side than a center of the front wall in a height direction thereof,
the upper tub part is supported by the lower tub part to be able to open the testing space, and
the frame members extend along the dividing surface in a direction inclined down and frontward.

* * * * *